United States Patent
Ozaki et al.

(10) Patent No.: US 9,719,929 B2
(45) Date of Patent: Aug. 1, 2017

(54) MICROARRAY ANALYSIS METHOD AND MICROARRAY READING DEVICE

(75) Inventors: Kumie Ozaki, Otsu (JP); Hiromichi Sasamoto, Otsu (JP); Kunihisa Nagino, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 548 days.

(21) Appl. No.: 13/981,787

(22) PCT Filed: Dec. 26, 2011

(86) PCT No.: PCT/JP2011/080007
§ 371 (c)(1),
(2), (4) Date: Jul. 25, 2013

(87) PCT Pub. No.: WO2012/101943
PCT Pub. Date: Aug. 2, 2012

(65) Prior Publication Data
US 2013/0303403 A1     Nov. 14, 2013

(30) Foreign Application Priority Data

Jan. 28, 2011   (JP) ................................ 2011-016690
Sep. 21, 2011   (JP) ................................ 2011-205865

(51) Int. Cl.
| | |
|---|---|
| G01N 33/48 | (2006.01) |
| G01N 33/50 | (2006.01) |
| G01N 21/64 | (2006.01) |
| G01N 33/543 | (2006.01) |
| G01N 33/58 | (2006.01) |
| G06F 19/20 | (2011.01) |
| C40B 60/12 | (2006.01) |

(52) U.S. Cl.
CPC ..... *G01N 21/6486* (2013.01); *G01N 21/6452* (2013.01); *G01N 33/54373* (2013.01); *G01N 33/582* (2013.01); *G06F 19/20* (2013.01); *B01J 2219/00529* (2013.01); *B01J 2219/00576* (2013.01); *B01J 2219/00693* (2013.01); *C40B 60/12* (2013.01); *G01N 21/6456* (2013.01)

(58) Field of Classification Search
None
See application file for complete search history.

(56) References Cited

U.S. PATENT DOCUMENTS

| | | | |
|---|---|---|---|
| 7,200,254 B2 | 4/2007 | Kira et al. | |
| 2003/0152255 A1 | 8/2003 | Kira et al. | |
| 2003/0152256 A1 | 8/2003 | Kira et al. | |
| 2006/0035220 A1 | 2/2006 | Tashiro et al. | |
| 2007/0037155 A1 | 2/2007 | Tashiro et al. | |
| 2011/0075937 A1* | 3/2011 | Tate | 382/218 |

FOREIGN PATENT DOCUMENTS

| | | |
|---|---|---|
| JP | 2003-156442 A | 5/2003 |
| JP | 2003-307518 A | 10/2003 |
| JP | 2005-024532 | 1/2005 |
| JP | 2005-049282 | 2/2005 |
| JP | 2005-172840 A | 6/2005 |
| JP | 2009068995 | 4/2009 |
| JP | 2010-526314 | 7/2010 |
| WO | WO2010/147167 A1 | 12/2010 |

OTHER PUBLICATIONS

English Machine Translation of JP 2005-024532 A [Jan. 27, 2005] 45 pages, translation obtained on Oct. 25, 2015.*
Japanese Notice of Allowance mailed Sep. 1, 2015 in Japanese Application No. 2011-205865.
International Search Report dated Feb. 7, 2012, application No. PCT/JP2011/080007.

* cited by examiner

*Primary Examiner* — Russell S Negin
(74) *Attorney, Agent, or Firm* — RatnerPrestia

(57) ABSTRACT

A microarray analysis method, in which a microarray obtained by arranging probes on a substrate surface having an irregular shape is irradiated with excitation light and fluorescence amounts of the probes excited by the excitation light are obtained as numerical data, includes a step (a) of measuring the fluorescence amounts of the probes to acquire fluorescence image data, a step (b) of receiving reflected light and/or scattered light from the substrate surface to acquire the irregular shape of the substrate surface of the microarray as alignment image data based on the light receiving intensities of the light, and a step (c) of determining positions of the probes on the fluorescence image data based on the alignment image data.

9 Claims, 11 Drawing Sheets

MICROARRAY ANALYSIS METHOD AND MICROARRAY READING DEVICE

CROSS REFERENCE TO RELATED APPLICATIONS

This application is the U.S. National Phase application of PCT International Application No. PCT/JP2011/080007, filed Dec. 26, 2011, and claims priority to Japanese Patent Application No. 2011-016690, filed Jan. 28, 2011, and Japanese Patent Application No. 2011-205865, filed Sep. 21, 2011, the disclosures of each application being incorporated herein by reference in their entireties for all purposes.

FIELD OF THE INVENTION

The present invention relates to a microarray analysis method and a microarray reading device.

BACKGROUND OF THE INVENTION

A technology called microarray has been advanced to be developed and used in biological, medical, and pharmaceutical fields since 1990. The microarray is obtained by immobilizing several tens to several tens of thousands of probes onto a substrate made of glass, plastic, or the like and applying a sample (target) labeled with fluorescent molecules or the like to the substrate so as to detect binding reaction between the probe and the sample with fluorescence or the like. The microarrays have a characteristic that makes it possible to perform comprehensive measurement at one time and are expected to be essential to personalized medicine in the future.

The probes to be immobilized onto the substrate include the following types and the microarrays are named based on the types of the probes. That is to say, well-known have been a DNA microarray (DNA chip) obtained by immobilizing DNAs as the probes onto the substrate, a protein microarray obtained by immobilizing proteins as the probes onto the substrate, a tissue microarray obtained by immobilizing a number of small specimens as the probes onto the substrate, a compound microarray obtained by immobilizing a number of low-molecular compounds as the probes onto the substrate, and the like.

Among them, the DNA microarray (hereinafter, referred to as DNA chip) has been put into practical use at the most advanced level. Studies have been performed actively on analyses of genes relating to diseases, and examination and diagnosis by using the genes and some of them have been put into practical use.

Described is the DNA chip as one mode of the microarray in detail below.

The DNA chip is obtained by spotting (immobilizing) DNAs onto the substrate made of glass, resin, or the like in a grid form. The DNAs (probe DNAs) as the probes that can react with the DNA sample to be labeled specifically are spotted on the DNA chip. Optically detectable luminescent or fluorescent mark is added to an unknown DNA sample to be analyzed. The unknown DNA sample to be analyzed is made to flow onto the DNA chip. With this, the DNA sample bonds to the spotted DNA to form a double strand if the unknown DNA sample and the spotted DNA have a complementary relation. Then, all the DNA samples that have not bonded to the probe DNAs are washed out, the DNA samples to be determined that remain on the DNA chip are made luminescent, and the DNA chip is read by a reading device (scanner). This makes it possible to observe the state of the double-stranded DNA as an image. That is to say, distribution of luminescent marks on the DNA chip is analyzed so as to analyze presence of the gene to be obtained, expression of a certain gene, or the degree of expression of the gene. In this manner, an already-known probe DNA set is configured on the DNA chip and the probe DNAs are mounted on a number of types of DNA chips so as to detect genetic alteration, an expression amount of the gene, and the like.

Hereinafter, FIG. 1 illustrates a series of processing processes of DNA chip analysis in detail.

In a preprocessing process as illustrated in FIG. 1, unknown DNA contained in a DNA sample extracted from a specimen is amplified and a fluorescent mark is added to the DNAs.

In the subsequent hybridization process, the DNA sample added with the fluorescent mark (for example, Cy3, Cy5, or the like) are made to drop onto the substrate of the DNA chip on which a number of types of probe DNA have been mounted. The DNA sample bonds to the spotted DNA to form a double strand if the DNA sample and the spotted DNA have a complementary relation.

Next, in the washing process, the hybridized DNA chip is washed with predetermined washer fluid. With this, all the DNA samples that have not bonded to the probe DNAs arranged in the grid form are washed out.

Subsequently, the washed DNA chip is scanned. In the scanning process, the DNA chip is irradiated with a laser beam having a predetermined wavelength suitable for exciting the fluorescent mark (for example, Cy3, Cy5, or the like) so as to be scanned in the reading device. With this, amounts of luminescence of the respective spotted DNAs (genes) are measured and fluorescence image data on which analysis processing is to be performed based on the amounts of luminescence is acquired.

In the analysis process, a fluorescence intensity of each spot is calculated by using a template for the obtained fluorescence image data and various types of analyses are executed.

FIG. 2 illustrates an example of a DNA chip 1 to be used for DNA chip analysis. The DNA chip 1 as illustrated in FIG. 2 includes blocks on a substrate 2. On each of the blocks, a predetermined number of probe DNAs corresponding to individual genes are arrayed in rows and columns in a matrix form (hereinafter, the probe DNA arranged on the block is referred to as a "spot" 3). It is to be noted that the spots 3 arranged on the substrate 2 correspond to genes of which base sequences have been already mapped and that are different from one another and arrangement positions of the spots 3 on the substrate 2 have been defined previously.

FIG. 3 illustrates an example of the template to be applied to the fluorescence image data of the DNA chip. As illustrated in FIG. 3, the template is divided into a plurality of blocks of 1 to 32, for example. Detection areas (corresponding to individual spots of the DNA chip) that are arranged in a matrix form of m rows×n columns (22×22 in FIG. 3) are provided on each block.

In the above-mentioned analysis process, the detection areas on the template provided by an analysis tool are assigned to the individual spots in the fluorescence image data read from a DNA chip (alignment) so as to calculate fluorescence intensities of the respective spots in the corresponding detection areas. In this case, the alignment processing needs to be executed accurately such that the individual detection areas of the template are set correctly to the individual spots on the image in order to execute accurate analysis.

The alignment method includes a pattern matching method and a projection method in which alignment is made on a block basis. As described in Patent Literature 1, alignment tries to be performed accurately by using a chip spotted with a fluorescent substance called positive control or a house-keeping gene contained in any specimens.

PATENT LITERATURE

Patent Literature 1: Japanese Laid-open Patent Publication No. 2005-172840

SUMMARY OF THE INVENTION

With any of the typical pattern matching method and projection method in which alignment is made on a block basis, alignment cannot be performed accurately unless an amount of hybridized sample DNAs is large and ¼ to approximately half spots that emit fluorescence having a sufficient intensity are present. When the sample extracted from the specimen contains a small amount of DNAs, alignment cannot be performed accurately in some cases. On the other hand, the method by arranging the fluorescent substance called positive control has an advantage that alignment can be performed even if spots that emit fluorescence having a sufficient intensity are less. The method, however, has problems in that the number of DNAs capable of being arranged is reduced and the cost is increased at the time of the chip manufacturing, for example. Furthermore, when the fluorescent substance is used as the positive control, the fluorescent substance liberates during the hybridization to contaminate the periphery of the positive control. This arises a risk that data cannot be obtained. Moreover, when the DNA probes corresponding to the house-keeping genes are arranged, if the sample extracted from the specimen contains a small amount of DNAs, fluorescence from the positive control is weak and it becomes difficult to perform alignment, as a result.

The present invention has been made in order to solve the above-mentioned problems and to provide an analysis method and an analysis device that make it possible to perform alignment processing appropriately in the analysis of a DNA chip on which no positive control is arranged or in the analysis of a chip in which a sample contains a small amount of DNAs.

The present invention has a characteristic of any one of the following configurations.

(1) A microarray analysis method in which a microarray obtained by arranging probes on a substrate surface having an irregular shape is irradiated with excitation light and fluorescence amounts of the probes excited by the excitation light are obtained as numerical data, the microarray analysis method including: a step (a) of measuring the fluorescence amounts of the probes to acquire fluorescence image data; a step (b) of receiving reflected light and/or scattered light from the substrate surface to acquire the irregular shape of the substrate surface of the microarray as alignment image data based on light receiving intensities of the light; and a step (c) of determining positions of the probes on the fluorescence image data based on the alignment image data.

(2) The microarray analysis method according to the above described (1), wherein the reflected light and/or the scattered light from the substrate surface is light from a light source emitting the excitation light that has been reflected and/or scattered by the microarray.

(3) The microarray analysis method according to the above described (1) or (2), wherein the step (c) includes: a step (c1) of detecting equal to or more than three reference points A of the microarray based on a difference in the light receiving intensities on the alignment image data; and a step (c2) of correcting strain of the fluorescence image data based on the detected reference points A.

(4) The microarray analysis method according to the above-described (3), wherein the step (c1) includes: a step (c1) of calculating a contour reference point a as points on a contour of the substrate on each of at least eight predetermined observation regions; a step (c2) of pairing at least two predetermined observation regions that are not overlapped as sets to obtain approximate straight lines with respect to a plurality of contour reference points a for the respective sets; and a step (c3) of calculating intersecting points of the approximate straight lines obtained for the respective sets to set the intersecting points as the reference points A.

(5) The microarray analysis method according to the above-described (3) or (4), wherein at the step (c2), array angles θx and θy of spots on which the probes are arranged are obtained from the reference points A and shear deformation strain of the fluorescence image data is corrected based on the array angles θx and θy of the spots and the following equations.

$$\begin{pmatrix} X \\ Y \end{pmatrix} = \begin{pmatrix} 1 & 0 \\ -\tan\theta xy & 1 \end{pmatrix} \begin{pmatrix} x \\ y \end{pmatrix} \quad (1)$$

$$\theta xy = \theta x - \theta y. \quad (2)$$

(6) The microarray analysis method according to any one of the above-described (3) to (5), wherein at the step (c1), four reference points A are detected, and when a quadrangular shape formed by connecting the four reference points A with straight lines is not a parallelogram, the quadrangular shape is made to approximate to a parallelogram and the vertices of the parallelogram are set as the reference points A again.

(7) The microarray analysis method according to any one of the above-described (1) to (6), wherein the microarray is a DNA microarray.

(8) A microarray reading device including: a laser light source that irradiates a microarray obtained by arranging probes on a substrate surface having an irregular shape with excitation light; an objective lens that makes a light flux of the excitation light reflected by the substrate surface and fluorescence from the probes be parallel light; an optical filter that cuts the excitation light reflected by the substrate surface and through which fluorescence from the probes penetrate; and an imaging lens and a detector that receive the fluorescence penetrated through the optical filter and acquire fluorescence image data, wherein the imaging lens and the detector receive light reflected and/or scattered by the substrate surface so as to acquire alignment image data on which the irregular shape of the substrate surface of the microarray is expressed, and the microarray reading device further comprises an arithmetic processing unit that detects positions of the probes on the fluorescence image data based on the alignment image data.

(9) The microarray reading device according to the above-described (8), wherein a pinhole restricting a subject depth is provided between the imaging lens and the detector.

According to the present invention, alignment processing can be performed appropriately even in the analysis of a DNA chip on which no positive control is arranged or in the analysis of a chip in which a sample contains a small amount of DNAs, thereby allowing analyses.

DESCRIPTION OF EMBODIMENTS OF THE INVENTION

A microarray analysis device according to the invention is a device that analyzes a DNA microarray (DNA chip) obtained by immobilizing DNAs as probes onto a substrate, a protein microarray obtained by immobilizing proteins as the probes onto the substrate, a tissue microarray obtained by immobilizing a number of small specimens onto the substrate, a compound microarray obtained by immobilizing a number of low-molecular compounds onto the substrate, and the like. The microarray analysis device performs alignment of fluorescence image data to be obtained by using an irregular shape of the substrate surface of the microarray. In the analysis device, the microarray on which probes are arranged on the substrate surface having the irregular shape is irradiated with excitation light so as to obtain fluorescence amounts from the respective probes excited with the excitation light as pieces of numerical data. In this case, the fluorescence amounts of the respective probes are measured to acquire fluorescence image data (step (a)). In addition to the step (a), reflected light and/or scattered light is/are received from the substrate surface so as to acquire the irregular shape of the substrate surface of the microarray as alignment image data based on the intensity of the received light (step (b)). Then, the positions of the respective probes on the fluorescence image data obtained at step (a) are determined based on the alignment image data obtained at step (b) (step (c)).

The microarray in the invention is obtained by immobilizing, for example, several tens to several tens of thousands of probes onto a substrate made of glass, plastic, or the like. The sample (target) labeled with fluorescent molecules or the like is applied to the substrate of the microarray so as to detect bonding reaction between the probes and the sample with fluorescence. As described above, the microarrays are named based on the types of the probes to be immobilized onto the substrate. That is to say, the microarrays include the DNA microarray (DNA chip) obtained by immobilizing DNAs as the probes onto the substrate, the protein microarray obtained by immobilizing proteins as the probes onto the substrate, the tissue microarray obtained by immobilizing a number of small specimens as the probes onto the substrate, and the compound microarray obtained by immobilizing a number of low-molecular compounds as the probes onto the substrate.

Hereinafter, the invention is described by using, as examples, an analysis method and an analysis device of a DNA chip as a representative example of the microarray.

Figure 1:
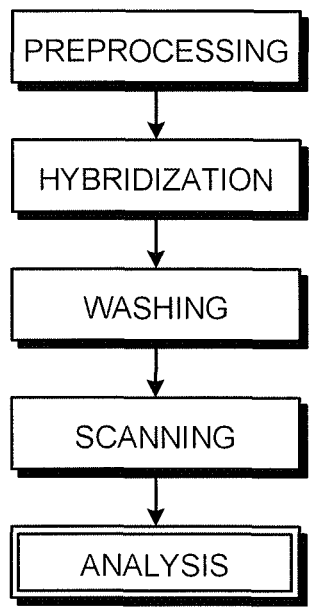
FIG. 1 is a schematic diagram illustrating a series of processes in DNA chip analysis.
Figure 2:
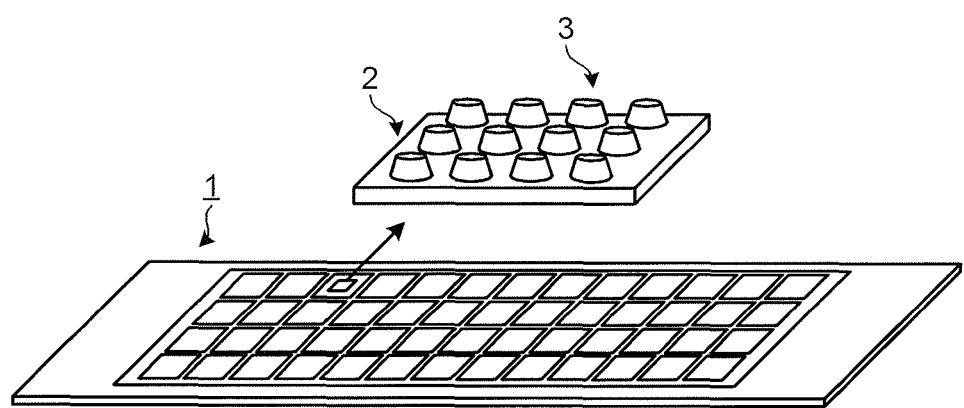
FIG. 2 is a schematic view illustrating an example of a DNA chip to be used in the DNA chip analysis.
Figure 3:
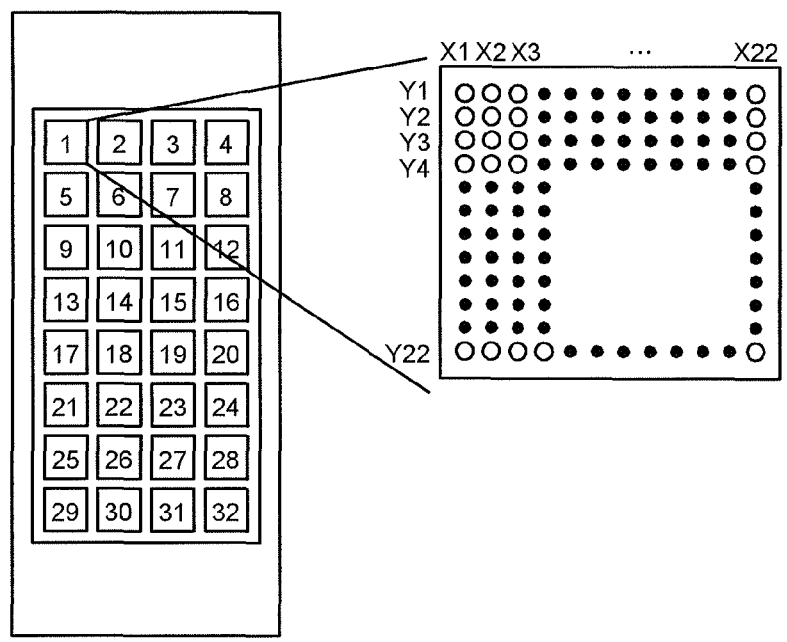
FIG. 3 is a plan view illustrating an example of a template to be applied to fluorescence image data of the DNA chip in the DNA chip analysis.
Figure 4:
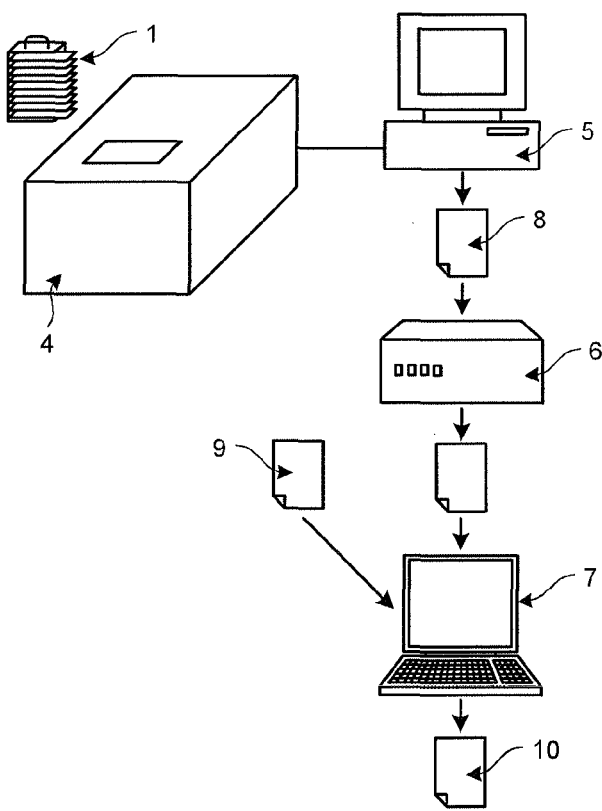
FIG. 4 is a schematic plan view illustrating a DNA chip analysis device as one embodiment of the invention.

The microarray such as the DNA chip is analyzed by using a scanner 4, a scanner control PC 5, an image server 6, an analysis PC 7, and the like, as illustrated in FIG. 4, for example.

Figure 5:
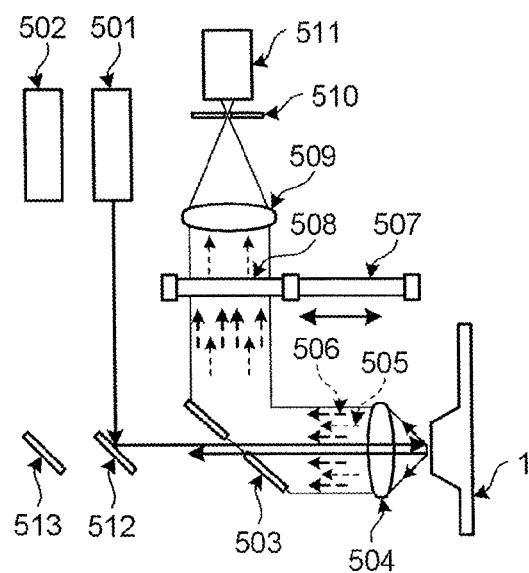
FIG. 5 is a schematic plan view illustrating an embodiment of an optical system in a DNA chip reading device.

The scanner 4 is constituted by a laser light source, an optical filter, an objective optical system, a detector that acquires fluorescence image data and alignment image data, and the like. To be more specific, the scanner 4 includes a scanning mechanism (not illustrated), an auto-loader mechanism (not illustrated), laser light sources 501 and 502, an objective lens 504, an excitation light cut filter 508, an excitation light cut filter 507, an imaging lens 509 and a detector 511, as illustrated in FIG. 5, for example. The scanning mechanism is a mechanism for scanning the substrate such as the DNA chip 1 in two directions (in the specification, the longitudinal direction of the chip is set to the y-axis direction and the direction orthogonal to the y-axis direction is set to the x-axis direction). A plurality of substrates such as the DNA chips are placed on the auto-loader mechanism. Each of the laser light sources 501 and 502 emits excitation light having a specific wavelength to the substrate surface. The objective lens 504 makes a light flux of light (fluorescence) from the probes that have received the excitation light and reflected light and scattered light of the excitation light from the substrate surface be parallel. The excitation light cut filter 508 cuts the excitation light from the laser light source 501 and makes the fluorescence from the probes penetrate therethrough. The excitation light cut filter 507 cuts the excitation light from the laser light source 502 and makes the fluorescence from the probes penetrate therethrough. The imaging lens 509 and the detector 511 receive and image the fluorescence from the probes so as to acquire the fluorescence image data. Furthermore, the imaging lens 509 and the detector 511 receive and image the reflected light and/or the scattered light from the substrate surface so as to acquire the irregular shape of the substrate surface of the microarray as the alignment image data based on the intensity of the received light.

It is to be noted that in the mode as illustrated in FIG. 5, the excitation light is made to be bent by a mirror 512 or 513 and to reach the DNA chip 1 in order to reduce the device in size.

The reference axes of the scanning mechanism are preferably orthogonal to each other in order to obtain an image with no strain. As the scanning mechanism, sliders are preferably used for two axes in general.

In the above-mentioned embodiment, the scanner 4 is configured as the device that adds two types of fluorescent marks to the DNA samples and reads these fluorescent marks. Based on the configuration, the scanner 4 includes the laser light sources 501 and 502 that emit light having wavelengths corresponding to the two types of fluorescent marks, respectively, and the excitation light cut filters 508 and 507 that correspond to the wavelengths of the excitation lights to be emitted, respectively. Alternatively, the scanner 4 may be configured as a device that adds only one type of fluorescent mark to the DNA sample and reads the fluorescent mark. Furthermore, the scanner 4 may be configured as a device that adds equal to or more than three types of fluorescent marks to the DNA samples and reads the fluorescent marks. In any cases, it is sufficient that laser light source(s) and excitation light cut filter(s) corresponding to the fluorescent dye(s) to be used is(are) provided.

A program that performs arithmetic processing for detecting the positions of the respective probes on the fluorescence image data based on the alignment image acquired by the detector 511 is introduced into the analysis PC 7 (arithmetic processing unit).

In the above-mentioned device, generally, the DNA chip onto which the DNA samples marked with fluorescent markers are made to drop is excited with the laser beam so as to acquire the fluorescence image data. When the fluorescence image data is acquired, the scanner control PC 5 controls scanning of the DNA chip 1 and image acquisition on the scanner 4. A general personal computer or the like is used as the scanner control PC 5.

The obtained fluorescence image data is stored in the image server 6 as a DNA chip image file 8. As will be described later, the DNA chip 1 is scanned with excitation wavelengths corresponding to the fluorescent dyes Cy3 and Cy5, for example, and pieces of fluorescence image data corresponding to the respective excitation wavelengths are obtained for one DNA chip 1. The pieces of fluorescence image data are stored in a file format such as a 16-bit gray scale Tiff format, a BMP format or a JPEG format, for example.

The analysis PC 7 loads the DNA chip image file 8 stored in the image server 6. Furthermore, the analysis PC 7 loads an analysis definition file 9 that defines a parameter for executing analysis and the like to execute analysis of an image of the DNA chip and output digitalized analysis result data as a digitalized data file 10. A program for executing analysis processing including alignment processing, which will be described later, is introduced into the analysis PC 7.

The microarray such as the DNA chip is analyzed by the above-mentioned method basically. In the invention, in addition to the process of acquiring the fluorescence image data (above-mentioned step (a)), reflected light and/or scattered light from the substrate surface of the microarray can be received so as to acquire the irregular shape of the substrate as alignment image data (above-mentioned step (b)). Then, the positions of the respective probes on the fluorescence image data are determined by the alignment processing based on the obtained alignment image data (above-mentioned step (c)).

Next, described is an acquisition method of the fluorescence image data and the alignment image data and an alignment processing method in the scanner 4 in detail.

First, described is the image acquiring method corresponding to the above-mentioned step (a) with reference to FIG. 5. Although described is the mode in which Cy5 and Cy3 are used as the fluorescent dyes below, any one of the fluorescent dyes for labeling the sample may be used and the fluorescent dye is not limited thereto. For example, Fluorescin, FITC, Alexa Fluor 555, Rodamine, Cy3.5, Texas Red, TAMURA, Oyster 650, Cy5.5, and the like can be used as the fluorescent dye.

For example, the laser light source 501 for Cy5 (light source of a laser beam having a wavelength of 635 nm, for example) emits a laser beam (that is, excitation light for the fluorescent dye Cy5) in order to load the fluorescent dye Cy5 first. The DNA chip 1 is irradiated with the laser beam through a perforated mirror 503 and the objective lens 504. Fluorescence 505 from the fluorescent molecules that emit light by excitation with the emitted laser beam and laser beam 506 reflected and/or scatted by chip surface are collected by the objective lens 504 so as to be substantially parallel with each other. Thereafter, the fluorescence 505 and the laser beam 506 are reflected by the perforated mirror 503 and are incident on the excitation light cut filter 508 for Cy5. It is to be noted that the laser beam that has been reflected by the chip surface regularly penetrates through the hole of the perforated mirror 503. The fluorescence 505 from the fluorescent molecules that emit light by excitation penetrates through the excitation light cut filter 508 and is collected by the imaging lens 509. On the other hand, the excitation light cut filter 508 cuts the excitation light (light reflected and/or scatted by the chip surface) that has reached the excitation light cut filter 508. The fluorescence 505 collected by the imaging lens 509 is incident on the detector 511 after light components thereof other than those in the vicinity of the focusing point of the imaging lens 509 are cut by a pinhole 510. The detector 511 outputs an electric signal in accordance with the intensity of the light. The processes are repeated while the scanner control PC 5 controls to scan the DNA chip 1 in the two directions and the electric signal output from the detector 511 is A/D-converted so as to create the fluorescence image data.

Subsequently, the fluorescent dye Cy3 is loaded. It is sufficient that the loading of the fluorescent dye Cy3 is performed in the same manner as the loading of the fluorescent dye Cy5 other than points that the laser light source 501 for Cy5 is replaced by the laser light source 502 for Cy3 (for example, light source of a laser beam having a laser wavelength of 532 nm) and the excitation light cut filter 508 for Cy5 is replaced by the excitation light cut filter 507 for Cy3. That is to say, the laser light source 502 for Cy3 emits the laser beam (that is, excitation light for the fluorescent dye Cy3) and the excitation light cut filter 507 for Cy3 removes the excitation light (that is, light reflected and/or scatted by the chip surface) that has reached the excitation light cut filter 507 so as to create the fluorescence image data as in the case of Cy5.

Figure 6:
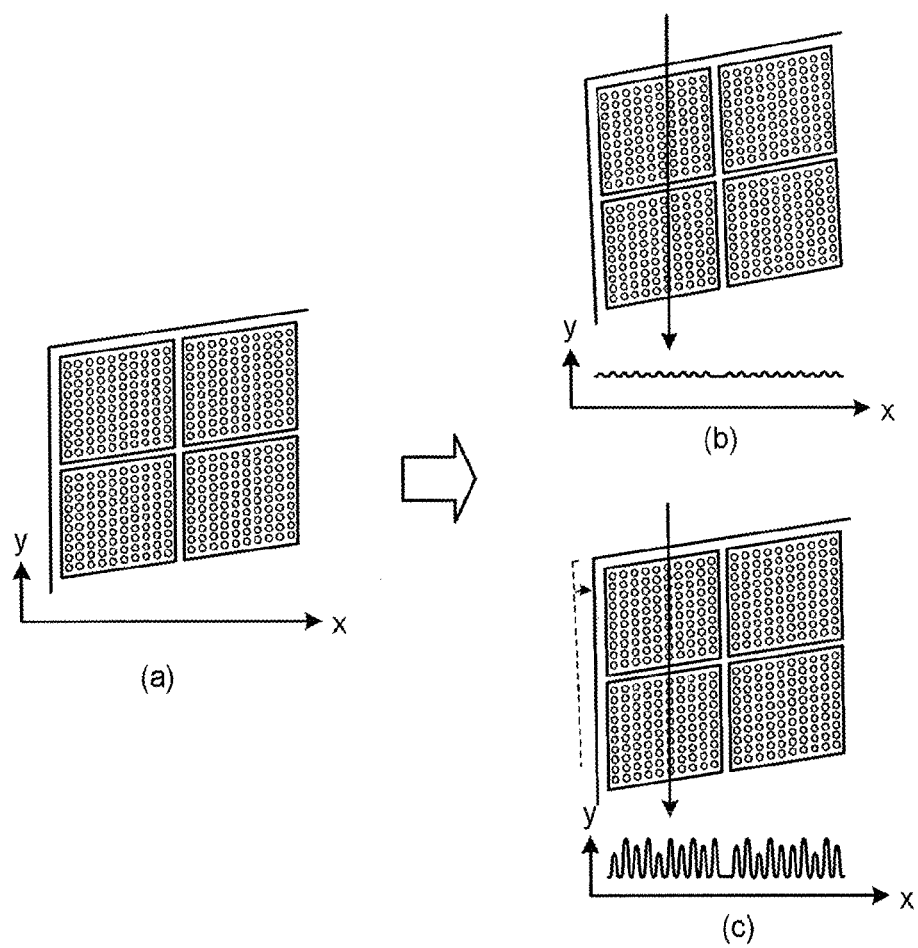
FIG. 6 is a plan view illustrating an example of fluorescence image data on which strain is generated and spot array is not perpendicular although a DNA chip on which the row direction and the columnar direction of the spot array are orthogonal to each other perpendicularly has been scanned.

Note that when the scanning mechanism of the scanner includes two sliders, these sliders are not necessarily orthogonal to each other. They are deviated from each other at the time of assembling the device, over time, or the like, in some cases. The image of the DNA chip read by the scanner is possibly inclined as illustrated in FIG. 6(*a*), for example. When the x-axis and the y-axis of the scanning mechanism are not orthogonal to each other as described above, the obtained fluorescence image data is strained, resulting in a problem in that the obtained image cannot be positioned rightly with respect to the detection areas of the template.

For solving this problem, it is preferable that the deviation in the orthogonal degree be detected from the image and be corrected so as to obtain an image equivalent to the image as obtained by the scanning mechanism in which the sliders are orthogonal to each other. To be more specific, the fluorescence image data is projected in the y-axis direction with respect to the x-axis so as to calculate an integrated intensity (integrated value of each pixel value) for each coordinate X. The processing is repeated while rotating the fluorescence image data about a point of origin in coordinates by a predetermined angle. An integrated intensity graph when the projecting direction and the array direction of the spots in the y-axis direction are deviated corresponds to a graph with no amplitude as illustrated in FIG. 6(b). On the other hand, an integrated intensity graph when the projecting direction and the array direction of the spots in the y-axis direction are identical corresponds to a graph with maximum signal amplitude as illustrated in FIG. 6(c). By using the characteristics of the projected data, an angle at which a standard deviation of the integrated intensity takes a maximum value is obtained so as to detect an array angle of the spots with respect to the y-axis. In the same manner, an array angle with respect to the x-axis is obtained and image processing such as shear deformation is performed, so that the array directions of the spots can be made to be orthogonal to each other.

When the fluorescence image data is acquired as described above, if the sample extracted from the specimen contains an extremely small amount of DNAs, the number of spots that emit light is reduced for Cy5 and Cy3, so that the boundary between blocks is not recognized. Furthermore, in that case, the orthogonal degree of the image cannot be corrected and the alignment processing cannot be performed.

In order to solve the problem, in one embodiment of the invention, in addition to the above-mentioned fluorescence image data, the following alignment image data is also acquired without resetting the chip (above-mentioned step (b)). That is to say, the DNA chip 1 is irradiated with light and the reflected light and/or the scattered light from the substrate surface of the chip is/are received so as to obtain alignment image data. With the processing, the reflected light and/or the scattered light from the substrate surface having the irregular shape is/are received actively and an image of the irregular shape of the substrate surface is made based on the intensity of the received light so as to use the irregular shape for alignment.

The spot positions on the DNA chip do not change until the DNA chip is reset. This indicates that the spot positions on the alignment image data and the spot positions on the pieces of fluorescence image data of Cy5 and Cy3 are identical to each other. In the invention, the alignment processing can be performed on the pieces of fluorescence image data by applying the alignment result obtained as the alignment image data to the pieces of fluorescence image data of Cy5 and Cy3.

Figure 7:
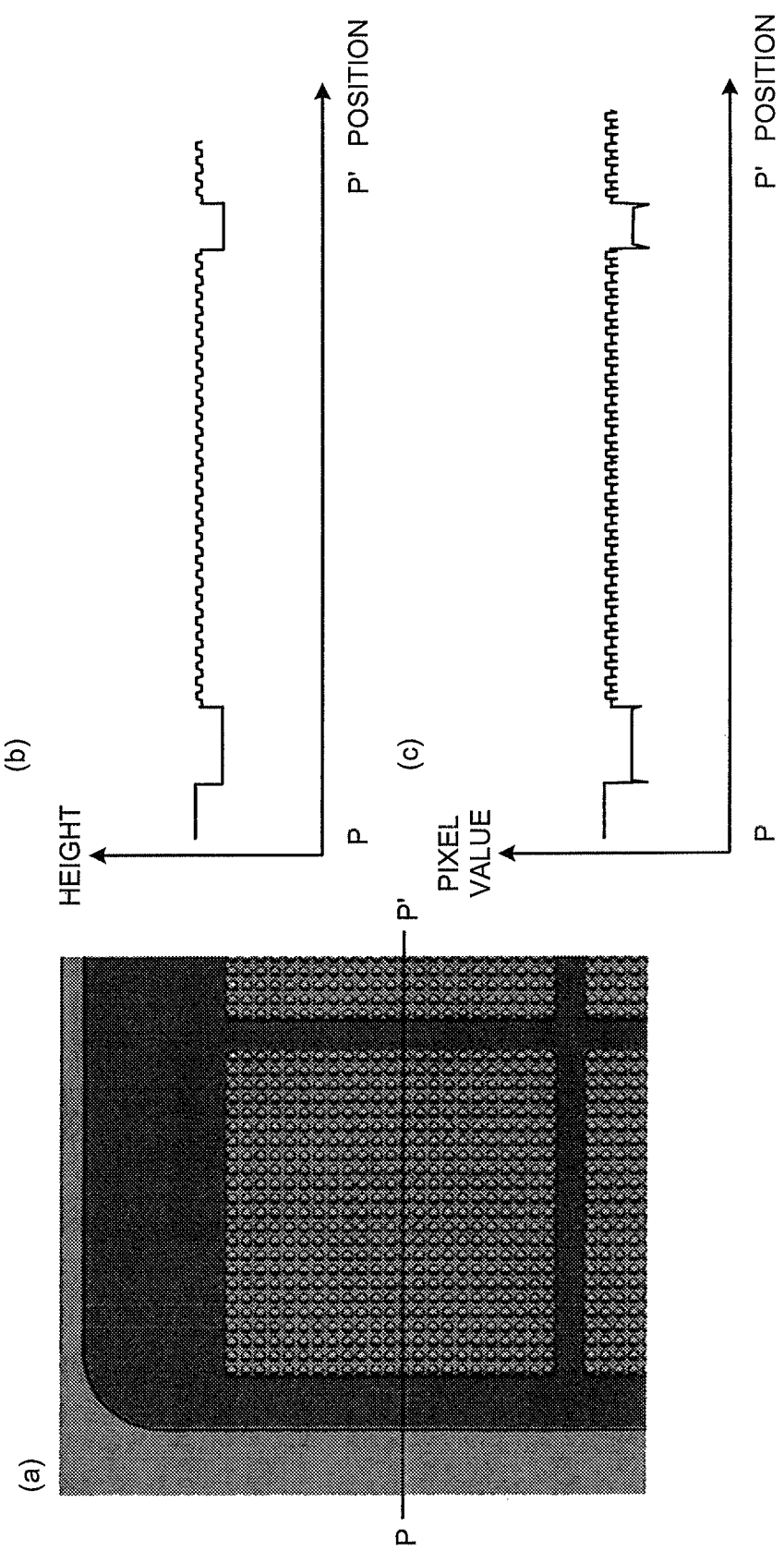
FIG. 7 is a view illustrating an example of an alignment image obtained by the DNA chip reading device.

In order to acquire the alignment image data in the device having the configuration as described above in practice, it is preferable that the laser light source 501 for Cy5 emit the laser beam and the excitation light cut filter 507 for Cy3 be used. In general, a band pass filter of 550 to 600 nm is used for the excitation light cut filter 507 for Cy3 in many cases. Since the excitation light for Cy5 having the wavelength (635 nm) penetrates through the excitation light cut filter 507 slightly in general (for example, an OD value of light having the wavelength of 635 nm is approximately 5), the irregular shape of the DNA chip can be imaged as illustrated in FIG. 7(a), for example. That is to say, received is not the fluorescence from the fluorescent molecules that emit light by excitation with the light having the specific wavelength but the reflected light and/or the scattered light from the substrate surface so as to make an image of the irregular shape of the substrate itself. FIG. 7(b) illustrates a profile of pixel values on a P-P' line segment in FIG. 7(a) and FIG. 7(c) illustrates a height profile of the DNA chip at the corresponding place. The laser beam is received actively in this manner, so that the intensity of the received light from the surface of the DNA chip in the vicinity of the focal point of the imaging lens 509 that is perpendicular to an optical axis of the laser beam is increased, thereby obtaining the alignment image data on which the irregular shape of the substrate surface is expressed as illustrated in FIG. 7(a).

Although a light source emitting excitation light for exciting the fluorescent molecules is preferably used for the light source for acquiring the alignment image data in order to reduce the number of parts of the scanner, there arises no problem if a light source for acquiring the alignment image data is provided additionally.

A method without using a filter when the alignment image data is acquired may be employed. When the filter is not used, a light amount incident on the detector becomes too large so as to generate a possibility that the detector is damaged. For this reason, when the laser light source 501 for Cy5 emits the laser beam, it is preferable that a filter through which light having the wavelength corresponding to the light source that emits light slightly penetrates be used, for example, the excitation light cut filter 507 be used as described above. In contrary, the laser light source 502 for Cy3 may emit the laser beam and the excitation light cut filter 508 may be used. Alternatively, an ND filter may be used instead of the excitation light cut filters 507 and 508, or the output of the laser beam itself may be made weaker so as to obtain the alignment image data without using the excitation light cut filters 507 and 508 and the ND filter. It is needless to say that a combination thereof can be employed.

For the alignment image data, there is a risk that rotational deviation and positional deviation are generated when the DNA chip is set on the scanner. In an embodiment of the invention, amounts of the rotational deviation and the positional deviation are also constant until the DNA chip is reset. This indicates that the spot positions on the alignment image data and the spot positions on the pieces of fluorescence image data of Cy5 and Cy3 are identical to each other.

Figure 8:
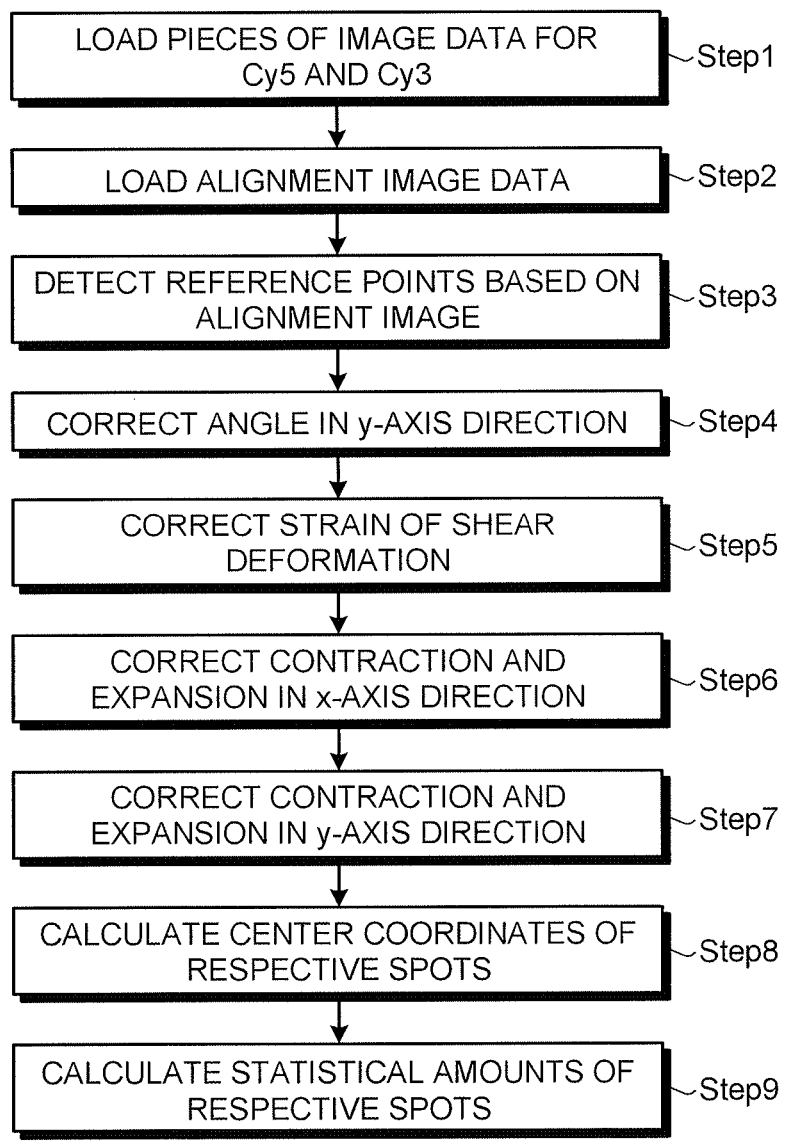
FIG. 8 is a block diagram illustrating one embodiment of a DNA chip analysis method.

Next, the positions of the respective probes on the pieces of fluorescence image data are determined based on the alignment image data (above-mentioned step (c)) to analyze the microarray. Hereinafter, detail description of the method is made with reference to the block diagram as illustrated in FIG. 8. Note that Steps 1 and 2 in FIG. 8 are processes corresponding to the above-mentioned processes.

First, at Step 1, the DNA chip is set on the scanner and pieces of fluorescence image data of the fluorescent dyes Cy5 and Cy3 are loaded as described above (above-mentioned step (a)). Subsequently, at Step 2, the laser light source 501 for Cy5 emits the excitation light and the excitation light cut filter 507 for Cy3 is used so as to load the alignment image while the DNA chip is kept to be set (above-mentioned step (b)). In this process, a configuration in which the laser light source 502 for Cy3 emits the excitation light and the excitation light cut filter 508 for Cy5 is used may be employed. Alternatively, a configuration in which another light source is prepared and reflected light and/or scattered light of the light from the DNA chip is/are received so as to acquire the alignment image may be employed.

Then, the positions of the respective probes on the pieces of fluorescence image data are determined by using the alignment image data at and after Step 3 (above-mentioned step (c)) so as to perform analysis.

Figure 9:
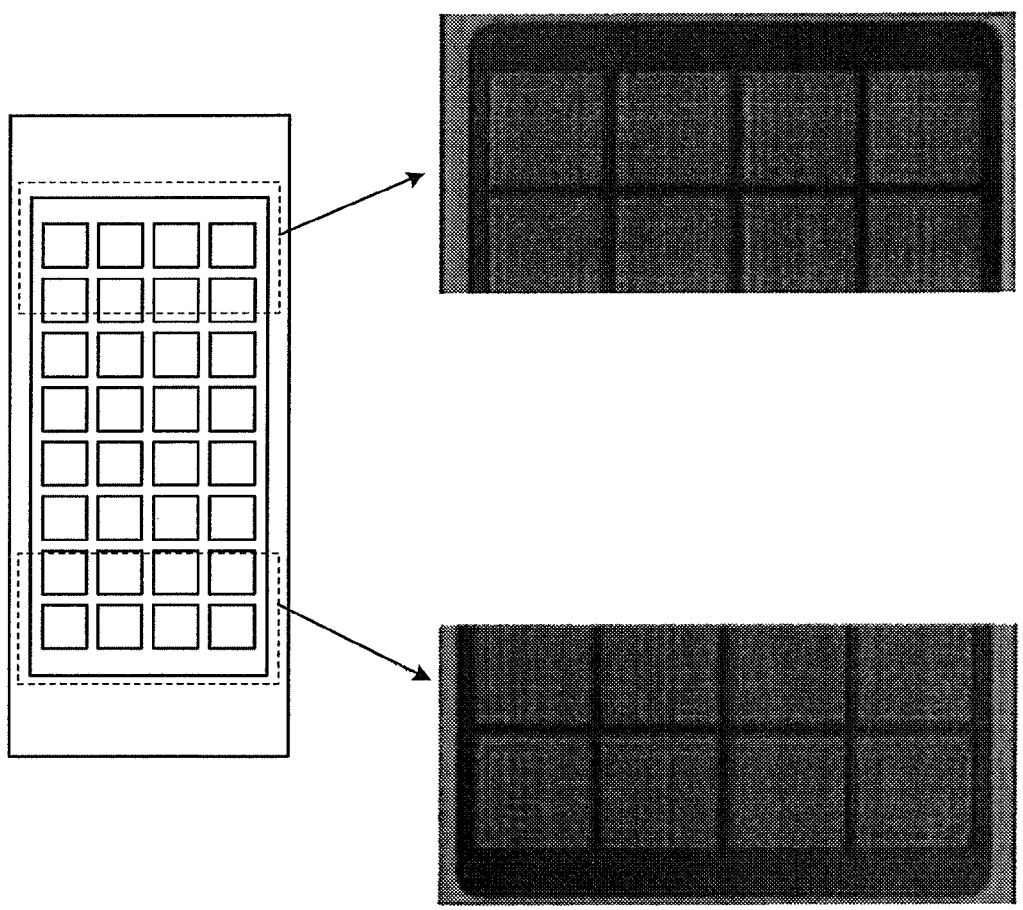
FIG. 9 is a view illustrating coordinates of four corners on the alignment image obtained by the DNA chip reading device.

To be more specific, first at Step 3, at least three reference points A on the alignment image data are detected (step (c1)). As the at least three reference points A, coordinates of four corners on the alignment image can be exemplified as illustrated in FIG. 9. As a method of detecting the coordinates of four corners, used is edge detection using light-dark information, pattern matching also using the light-dark information while images at four corners are set to master images, or the like, desirably.

Subsequently, at Steps 4 and 5, strains of the pieces of fluorescence image data are corrected based on the reference points A (step (c2)).

Figure 10:
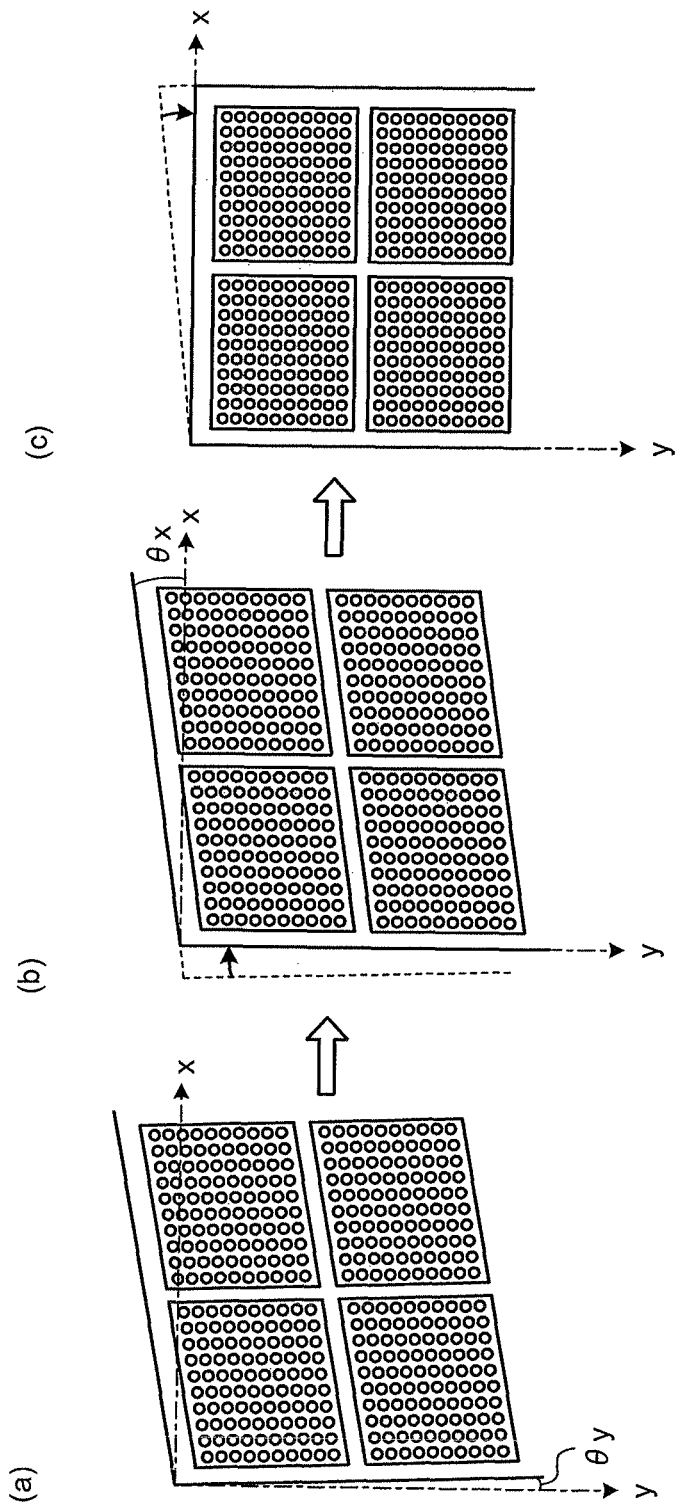
FIG. 10 is a view illustrating processing at Step 4 and Step 5 in FIG. 8.

To be more specific, at Step 4, an array angle θx of the spots (inclination angle of a line connecting the most adjacent spots linearly with respect to the x-axis) with respect to the x-axis and an array angle θy of the spots (inclination angle of a line connecting the most adjacent spots linearly with respect to the y-axis) with respect to the y-axis are detected from the above-mentioned coordinates of four corners, for example. It is desirable that θx and θy take average values of angles of two line segments for the corresponding directions among four line segments connecting the coordinates of four corners. It is to be noted that even if the reference points are three, θx and θy can be calculated. Then, as illustrated in FIGS. 10(a) and 10(b), each fluorescence image data is rotated by using the array angle θy of the spots with respect to the y-axis as a correction angle, so that the spots are made to be parallel with the y-axis.

Furthermore, at Step 5, conversion (shear deformation) is executed on the rotated image based on the array angles θx and θy of the spots aligned regularly in the two directions that have been detected as described above and the following equations. With this, strain of the shear deformation on the image is corrected. The converted image is illustrated in FIG. 10(c). It is to be noted that (x, y) in the following equation corresponds to coordinates before conversion and (X, Y) corresponds to coordinates after conversion. Furthermore, θxy corresponding to the deviation of the scanning mechanism of the scanner (orthogonal degree of the reference axes of the scanning mechanism) is obtained by subtracting the array angle θy of the spots with respect to the y-axis from the array angle θx of the spots with respect to the x-axis as illustrated in Equation 4.

$$\begin{pmatrix} X \\ Y \end{pmatrix} = \begin{pmatrix} 1 & 0 \\ -\tan\theta_{xy} & 1 \end{pmatrix} \begin{pmatrix} x \\ y \end{pmatrix} \quad (3)$$

$$\theta_{xy} = \theta_x - \theta_y \quad (4)$$

Furthermore, when the DNA chip 1 is a resin mold, the resin expands with moisture absorption and temperature change in the hybridization process and the washing process in some cases. Depending on the processing time in each process, the resin expands by several tens μm in some cases to give an influence on accuracy of alignment.

For this reason, the chip lengths in the x-axis direction and in the y-axis direction are calculated from the above-mentioned coordinates of four corners at Steps 6 and 7, for example, and each fluorescence image data is contracted such that the chip length is identical to a designed value.

Figure 11:
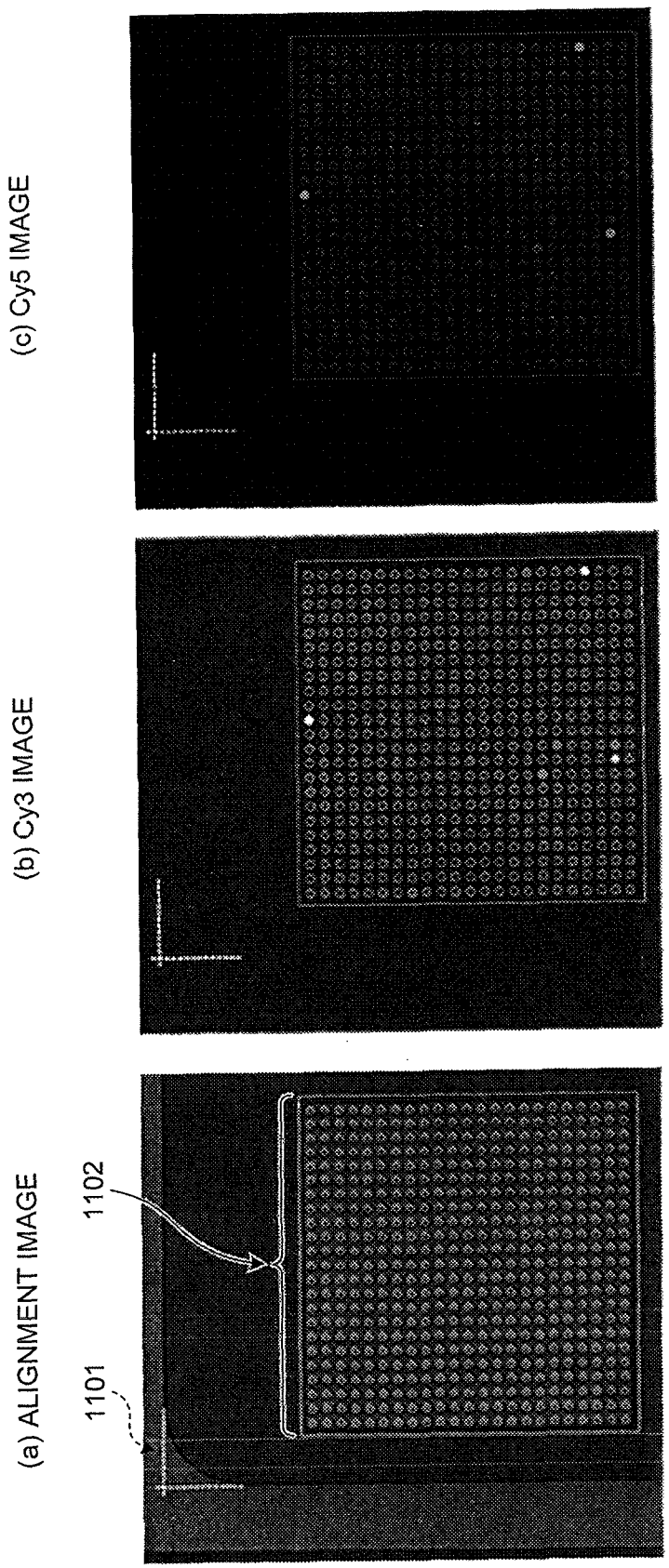
FIG. 11 is a view illustrating examples of the alignment image data (a) and fluorescence image data (b) and (c) subjected to analysis in the invention.

Subsequently, alignment is performed on each fluorescence image data on which rotational correction, shear deformation correction, and contraction correction have been performed as described above. The pieces of positional information of the respective spots on the template that has been stored in the analysis definition file previously indicate center coordinates of the spots while an upper left corner of the chip is set to a point of origin, for example. Alignment can be performed on each image after the contraction correction has been performed at Step 7 as illustrated in FIGS. 11(b) and 11(c) by calculating each spot frame while setting the coordinates of the upper left corner to the point of origin, for example (Step 8). It is to be noted that FIG. 11(b) illustrates an image indicating a result of the alignment performed on the fluorescence image data of Cy3 and FIG. 11(c) illustrates an image indicating a result of the alignment performed on the fluorescence image data of Cy5. Furthermore, FIG. 11(a) illustrates an image indicating a result of the alignment performed on the alignment image data obtained at Step 2 as a reference. In the drawings, inner portions of circles drawn by dashed lines are detection areas defined by the template.

Thereafter, at Step 9, statistical amounts such as average values, median values, and standard deviations, for the signal intensities of pixels within the spot radius are calculated from the center coordinates of the respective spots that have been obtained at Step 8. Then, the respective pieces of numerical data in addition to block numbers to which the spots belong, matrix numbers of the spots, and arranged probe DNA names are output as files.

It is to be noted that the order of the above-mentioned Steps 1 and 2 may be switched in the process as illustrated in FIG. 8.

Furthermore, the four corners of the DNA chip are molded to be rounded in order to improve fluidity of the specimen at the time of the hybridization in some cases. The reference points A are desirably detected based on the coordinates of points on a contour of the DNA chip when the reference points A are detected at Step 3.

Figure 12:
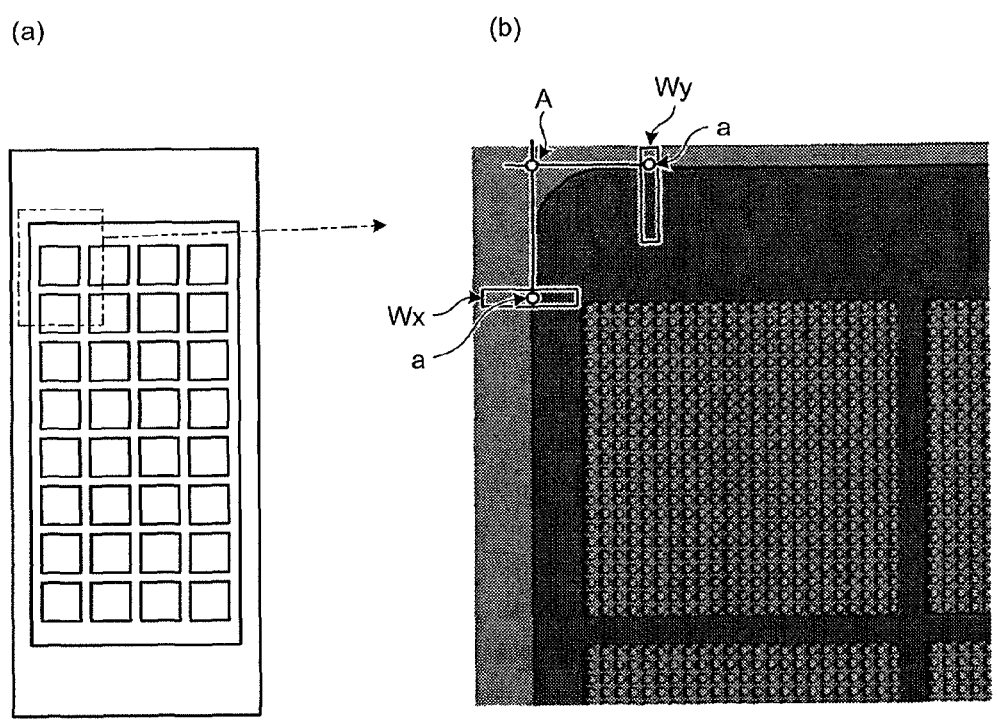
FIG. 12 is a view illustrating an example of a method of detecting reference points.

That is to say, as illustrated in FIG. 12, a contour point detection window (observation region) Wy containing a contour extending to the x-axis direction substantively and a contour point detection window Wx containing a contour extending to the y-axis direction substantively are set in the vicinity of each of the four corners of the DNA chip. Then, a contour reference point a corresponding one point on the contour of the DNA chip is detected on each of the contour point detection windows Wx and Wy. Thereafter, coordinates of the reference point A corresponding to the corner of the DNA chip are calculated from the y coordinate of the contour reference point a on the window Wy and the x coordinate of the contour reference point a in the window Wx. This processing is performed for four corners, for example.

Figure 13:
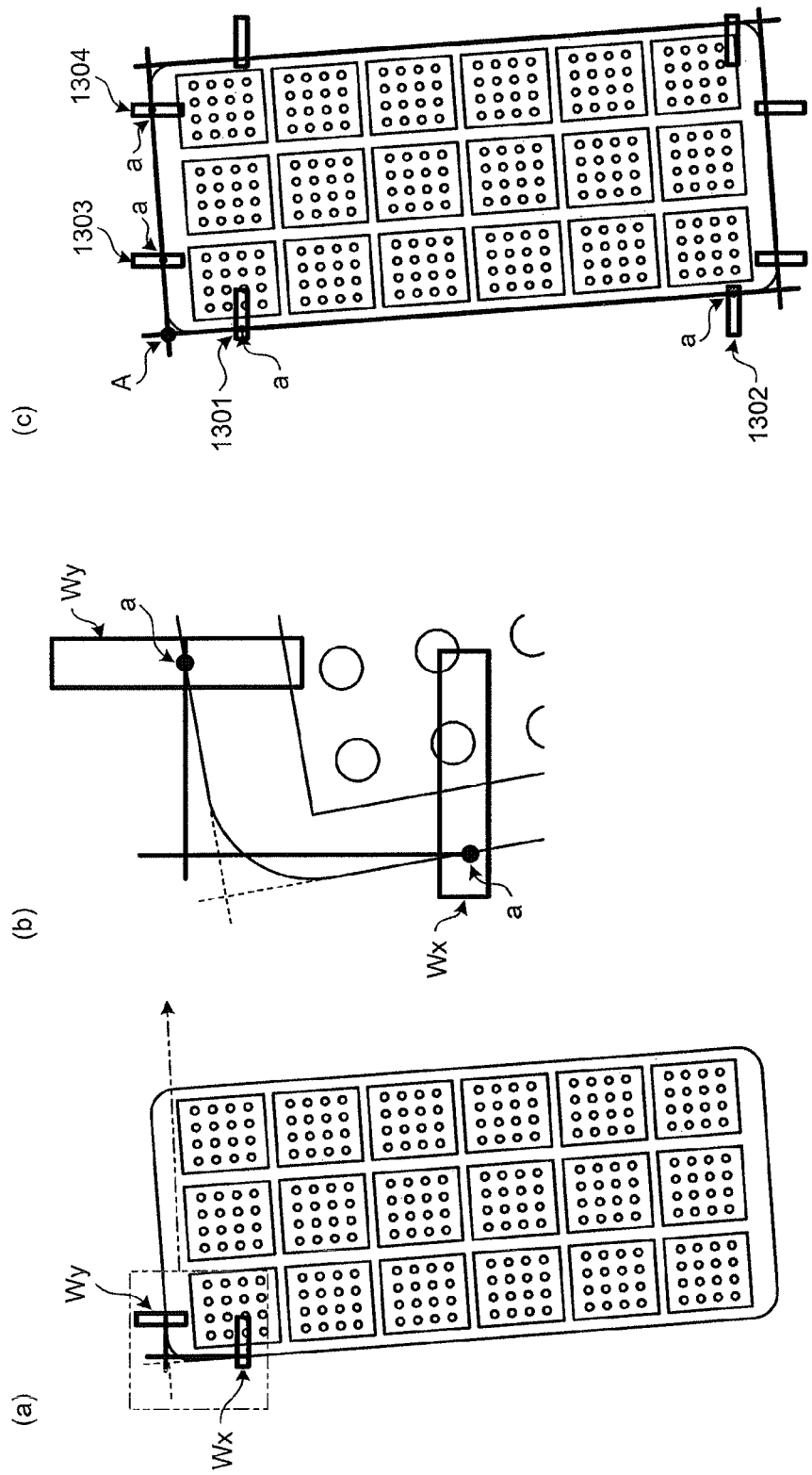
FIG. 13 is a view when the DNA chip is rotated on the alignment image data.

Furthermore, when only one contour point detection window Wx and one contour point detection window Wy are set for each of the four corners, if the DNA chip is fixed to a fixing jig of the scanner obliquely, error is generated between the position of the reference point A to be detected and the position of the reference point A detected actually as illustrated in FIG. 13(a) and FIG. 13(b). Note that in FIG. 13(b), the portion surrounded by the two-dot chain line in FIG. 13(a) is enlarged. Due to the error, the spots cannot be aligned desirably.

In order to solve this, in the invention, it is preferable that at least four contour point detection windows Wx and four contour point detection windows Wy, that is, equal to or more than eight contour point detection windows in total be set. To be more specific, as illustrated in FIG. 13(c), it is preferable that at least two contour point detection windows Wx (1301 and 1302) and at least two contour point detection windows Wy (1303 and 1304) be set for each of the four corners (step (c11)).

For each of the four corners, at least two contour point detection windows Wx (1301 and 1302) are paired as a set and an approximate straight line with respect to a plurality of contour reference points a on the set is obtained, and at least two contour point detection windows Wy (1303 and 1304) are paired as a set and an approximate straight line with respect to a plurality of contour reference points a on the set is obtained (step (c12)). An intersecting point of two approximate straight lines obtained in this manner is obtained so as to be set as the reference point A (step (c13)).

With this, the reference points A can be detected with high accuracy even when the chip is fixed obliquely.

In the invention, the reference points A are not necessarily required to be obtained on the four corners and it is sufficient that the reference points A are obtained on the three corners.

Furthermore, when the reference points A are detected as described above, measurement error is generated if scratches or dusts are present on the detector. Due to this, even if four reference points A corresponding to four corners of the substrate are detected, a shape formed by connecting these four reference points A is not a parallelogram (including rectangle shape and square shape) but a quadrangular shape such as a trapezoidal shape in some cases. The correction of the shear deformation strain at the subsequent processing Step 5 is performed with the assumption that the shape formed by the detected reference points is the parallelogram. This arises a risk that the spots cannot be aligned desirably in the above-mentioned case.

Figure 14:
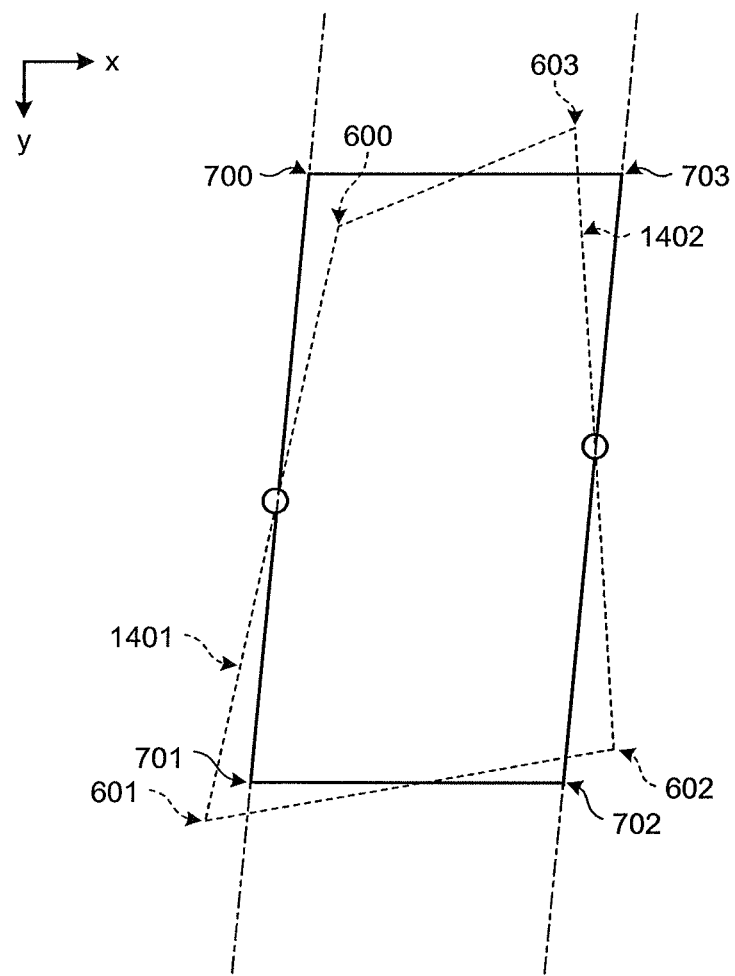
FIG. 14 is a view illustrating a method of approximating a trapezoidal shape to a parallelogram.

For solving this, in the invention, as illustrated in FIG. 14, the quadrangular shape formed by the four reference points A 600 to 603 detected once is not the parallelogram (including rectangle shape and square shape), it is preferable that the shape be made to approximate to a parallelogram and the vertices of the approximated parallelogram be set as the reference points A 700 to 703 again.

For making the quadrangular shape formed by the four reference points A 600 to 603 detected first approximate to a parallelogram, an average of slopes of two line segments 1401 and 1402 as opposite sides and the respective intermediate points of the line segments 1401 and 1402 are obtained. Then, two straight lines passing through the intermediate points and having the average slope are obtained. This processing is performed for other two line segments in the same manner and the intersecting points of the obtained four straight lines are set as the reference points A 700 to 703 again after approximation to the parallelogram. With this, even if the measurement error is generated on the reference points detected once, alignment can be performed with high accuracy.

In an embodiment of the invention, the fluorescence image data obtained based on the gene expression is processed in the above manner to acquire desired numerical data. The various types of numerical data thus obtained are used for analyzing presence of the gene to be obtained, expression of a certain gene, or the degree of expression of the gene, and so on.

Furthermore, in the above-mentioned analysis of the DNA chip, correction and alignment of the image are performed by using irregularities of the DNA chip. Positioning processing of the detection areas arranged on the substrate of the DNA chip can be also executed with high accuracy even for an image on which the sample extracted from the specimen contains a small amount of DNAs and spots emitting light are less and an image obtained by a reading device in which accuracy of the scanning mechanism is bad.

In the above-mentioned embodiment, described has been the embodiment of the DNA chip on which DNAs have been spotted onto the microarray. The invention can be also applied to a chip on which RNAs, proteins, small specimens, low-molecular compounds, cells, or the like are spotted.

For example, the same method can be used even in the case where proteins (antibodies) instead of the DNAs are immobilized onto the substrate of the DNA chip having the irregular shape as described above and presence or absence of reaction with a specimen and quantification are detected with fluorescence. There are the case where proteins present in a sample cell lysate are labeled with Cy5 and proteins present in a control cell lysate are labeled with Cy3 and they are mixed to react with the antibody array, and the method where proteins are labeled with biotin instead of the fluorescence and they are bonded to the antibody array, and then, a signal is sensitized by using enzyme-labeled avidin. Even in these cases, the invention makes it possible to perform alignment with high accuracy and output various types of numerical data of fluorescence intensities as files. In the case of the RNA array, the method can be used when hybridization of the RNAs immobilized onto the substrate having the irregular shape and the fluorescence-labeled DNAs or RNAs is detected with fluorescence. In the cases of the small specimens and the cell arrays, the invention can be applied when the bonding reaction between the small specimens or the cells immobilized onto the substrate having the irregular shape and the fluorescence-labeled specimen (for example, antibody) is detected with fluorescence.

REFERENCE SIGNS LIST

1 DNA CHIP
2 SUBSTRATE
3 SPOT
4 SCANNER
5 SCANNER CONTROL PC
6 IMAGE SERVER
7 ANALYSIS PC
8 DNA CHIP IMAGE FILE
9 ANALYSIS DEFINITION FILE
10 NUMERICAL DATA FILE
501 LASER LIGHT SOURCE (FOR Cy5)
502 LASER LIGHT SOURCE (FOR Cy3)
503 PERFORATED MIRROR
504 OBJECTIVE LENS
505 FLUORESCENCE FROM FLUORESCENT MOLECULES
506 LASER BEAM REFLECTED AND/OR SCATTERED FROM SUBSTRATE SURFACE
507 EXCITATION LIGHT CUT FILTER (FOR Cy3)
508 EXCITATION LIGHT CUT FILTER (FOR Cy5)
509 IMAGING LENS
510 PINHOLE
511 DETECTOR
512 MIRROR
513 MIRROR
600 TO 603 REFERENCE POINT A DETECTED ONCE
700 TO 703 REFERENCE POINT A AFTER APPROXIMATION TO PARALLELOGRAM
1101 REFERENCE POINT OF ALIGNMENT IMAGE
1102 CALCULATED SPOT FRAME

1301, 1302 CONTOUR POINT DETECTION WINDOW WX
1303, 1304 CONTOUR POINT DETECTION WINDOW WY
1401 TO 1402 LINE SEGMENT

The invention claimed is:

1. A microarray analysis method in which a microarray obtained by arranging probes on a substrate surface having an irregular shape is irradiated with excitation light and fluorescence amounts of the probes excited by the excitation light are obtained as numerical data, the microarray analysis method comprising:
  immobilizing probes onto a substrate surface having an irregular shape to obtain a microarray, wherein the probes are selected from the group consisting of DNA, RNA, proteins, tissues, and low-molecular compounds;
  a step (a) for measuring the fluorescence amounts of the probes to acquire fluorescence image data;
  a step (b) for receiving reflected light and/or scattered light from the substrate surface to acquire the irregular shape of the substrate surface of the microarray as alignment image data based on light receiving intensities of the light;
  a step (c) for determining positions of the probes on the fluorescence image data based on the alignment image data,
  wherein the step (c) comprises:
  a step (c1) for detecting equal to or more than three reference points A of the microarray based on a difference in the light receiving intensities on the alignment image data, wherein step (c1) comprises:
    a step of calculating a contour reference point a as points on a contour of the substrate on each of at least eight predetermined observation regions;
    a step of pairing at least two predetermined observation regions that are not overlapped as sets to obtain approximate straight lines with respect to a plurality of contour reference points A for the respective sets; and
    a step of calculating intersecting points of the approximate straight lines obtained for the respective sets to set the intersecting points as the reference points A; and
  a step (c2) for correcting shear deformation strain of the fluorescence image data based on the detected reference points A and to provide a corrected fluorescence image.

2. The microarray analysis method according to claim 1, wherein the reflected light and/or the scattered light from the substrate surface is light from a light source emitting the excitation light that has been reflected and/or scattered by the microarray.

3. The microarray analysis method according to claim 1, wherein the microarray is a DNA microarray.

4. A microarray analysis method in which a microarray obtained by arranging probes on a substrate surface having an irregular shape is irradiated with excitation light and fluorescence amounts of the probes excited by the excitation light are obtained as numerical data, the microarray analysis method comprising:
  a step (a) for measuring the fluorescence amounts of the probes to acquire fluorescence image data;
  a step (b) for receiving reflected light and/or scattered light from the substrate surface to acquire the irregular shape of the substrate surface of the microarray as alignment image data based on light receiving intensities of the light;
  a step (c) for determining positions of the probes on the fluorescence image data based on the alignment image data,
  wherein the step (c) comprises:
  a step (c1) for detecting equal to or more than three reference points A of the microarray based on a difference in the light receiving intensities on the alignment image data; and
  a step (c2) for correcting shear deformation strain of the fluorescence image data based on the detected reference points A and to provide a corrected fluorescence image, wherein at the step (c2), array angles $\theta x$ and $\theta y$ of spots on which the probes are arranged are obtained from the reference points A and shear deformation strain of the fluorescence image data is corrected based on the array angles $\theta x$ and $\theta y$ of the spots and the following equations:

$$\begin{pmatrix} X \\ Y \end{pmatrix} = \begin{pmatrix} 1 & 0 \\ -\tan\theta xy & 1 \end{pmatrix} \begin{pmatrix} x \\ y \end{pmatrix}$$

$$\theta xy = \theta x - \theta y$$

wherein (x,y) corresponds to coordinates before correction and (X,Y) corresponds to coordinates after correction, array angle $\theta x$ is an inclination angle of a line connecting most adjacent spots linearly with respect to the x-axis, array angle $\theta y$ is the inclination angle of a line connection most adjacent spots linearly with respect to the y-axis,
wherein the probes are selected from the group consisting of DNA, RNA, proteins, tissues, and low-molecular compounds.

5. A microarray analysis method in which a microarray obtained by arranging probes on a substrate surface having an irregular shape is irradiated with excitation light and fluorescence amounts of the probes excited by the excitation light are obtained as numerical data, the microarray analysis method comprising:
  immobilizing probes onto a substrate surface having an irregular shape to obtain a microarray, wherein the probes are selected from the group consisting of DNA, RNA, proteins, tissues, and low-molecular compounds;
  a step (a) for measuring the fluorescence amounts of the probes to acquire fluorescence image data;
  a step (b) for receiving reflected light and/or scattered light from the substrate surface to acquire the irregular shape of the substrate surface of the microarray as alignment image data based on light receiving intensities of the light;
  a step (c) for determining positions of the probes on the fluorescence image data based on the alignment image data,
  wherein the step (c) comprises:
  a step (c1) for detecting four reference points A of the microarray based on a difference in the light receiving intensities on the alignment image data, and when a quadrangular shape formed by connecting the four reference points A with straight lines is not a parallelogram, the quadrangular shape is made to approximate to a parallelogram and the vertices of the parallelogram are set as the reference points A again; and
  a step (c2) for correcting shear deformation strain of the fluorescence image data based on the detected reference points A and to provide a corrected fluorescence image.

6. A microarray reading device comprising:
a laser light source that irradiates a microarray obtained by arranging probes on a substrate surface having an irregular shape with excitation light;
an objective lens that makes a light flux of the excitation light reflected by the substrate surface and fluorescence from the probes be parallel light;
an optical filter that cuts the excitation light reflected by the substrate surface and through which fluorescence from the probes penetrate; and
an imaging lens and a detector that receive the fluorescence penetrated through the optical filter and acquire fluorescence image data,
the imaging lens and the detector receiving light reflected and/or scattered by the substrate surface so as to acquire alignment image data on which the irregular shape of the substrate surface of the microarray is expressed; and
a processor that detects positions of the probes on the fluorescence image data based on the alignment image data, wherein the processor is configured to detect three or more reference points A of the microarray based on a difference in the light receiving intensities on the alignment image data by calculating a contour reference point a as points on a contour of the substrate on each of at least eight predetermined observation regions, pairing at least two predetermined observation regions that are not overlapped as sets to obtain approximate straight lines with respect to a plurality of contour reference points A for the respective sets, and calculating intersecting points of the approximate straight lines obtained for the respective sets to set the intersecting points as the reference points A, and correcting shear deformation strain of the fluorescence image data based on the detected reference points A and provides a corrected fluorescence image
wherein the probes are selected from the group consisting of DNA, RNA, proteins, tissues, and low-molecular compounds.

7. The microarray reading device according to claim 6, wherein a pinhole restricting a subject depth is provided between the imaging lens and the detector.

8. A microarray reading device comprising:
a laser light source that irradiates a microarray obtained by arranging probes on a substrate surface having an irregular shape with excitation light;
an objective lens that makes a light flux of the excitation light reflected by the substrate surface and fluorescence from the probes be parallel light;
an optical filter that cuts the excitation light reflected by the substrate surface and through which fluorescence from the probes penetrate; and
an imaging lens and a detector that receive the fluorescence penetrated through the optical filter and acquire fluorescence image data,
the imaging lens and the detector receiving light reflected and/or scattered by the substrate surface so as to acquire alignment image data on which the irregular shape of the substrate surface of the microarray is expressed; and
a processor that detects positions of the probes on the fluorescence image data based on the alignment image data, wherein the processor is configured to detect three or more reference points A of the microarray based on a difference in the light receiving intensities on the alignment image data and to correct shear deformation strain of the fluorescence image data based on the detected reference points A and to provide a corrected fluorescence image, wherein array angles θx and θy of spots on which the probes are arranged are obtained from the reference points A and shear deformation strain of the fluorescence image data is corrected based on the array angles θx and θy of the spots and the following equations:

$$\begin{pmatrix} X \\ Y \end{pmatrix} = \begin{pmatrix} 1 & 0 \\ -\tan\theta xy & 1 \end{pmatrix} \begin{pmatrix} x \\ y \end{pmatrix}$$

$$\theta xy = \theta x - \theta y$$

wherein (x,y) corresponds to coordinates before correction and (X,Y) corresponds to coordinates after correction, array angle θx is an inclination angle of a line connecting most adjacent spots linearly with respect to the x-axis, array angle θy is the inclination angle of a line connection most adjacent spots linearly with respect to the y-axis;
wherein the probes are selected from the group consisting of DNA, RNA, proteins, tissues, and low-molecular compounds.

9. A microarray reading device comprising:
a laser light source that irradiates a microarray obtained by arranging probes on a substrate surface having an irregular shape with excitation light;
an objective lens that makes a light flux of the excitation light reflected by the substrate surface and fluorescence from the probes be parallel light;
an optical filter that cuts the excitation light reflected by the substrate surface and through which fluorescence from the probes penetrate; and
an imaging lens and a detector that receive the fluorescence penetrated through the optical filter and acquire fluorescence image data,
the imaging lens and the detector receiving light reflected and/or scattered by the substrate surface so as to acquire alignment image data on which the irregular shape of the substrate surface of the microarray is expressed; and
a processor that detects positions of the probes on the fluorescence image data based on the alignment image data, wherein the processor is configured to detect four reference points A of the microarray based on a difference in the light receiving intensities on the alignment image data and form a quadrangular shape that is not a parallelogram by connecting the four reference points A with straight lines and making the quadrangular shape approximate a parallelogram and setting the vertices of the parallelogram as the reference points A, and to correct shear deformation strain of the fluorescence image data based on the reference points A of the parallelogram and to provide a corrected fluorescence image;
wherein the probes are selected from the group consisting of DNA, RNA, proteins, tissues, and low-molecular compounds.

* * * * *